US006713080B1

(12) United States Patent
Aiache et al.

(10) Patent No.: US 6,713,080 B1
(45) Date of Patent: Mar. 30, 2004

(54) INTRAOCULAR LENS CONTAINING RELEASABLE MEDICATION

(75) Inventors: Jean-Marc Aiache, Clermont-Ferrand (FR); Gilbert Serpin, Clermont-Ferrand (FR); Said El Meski, Beaumont (FR); Philippe Tourrette, Clavette (FR)

(73) Assignee: Ioltechnologie-Production, La Rochelle (FR)

( * ) Notice: Subject to any disclaimer, the term of this patent is extended or adjusted under 35 U.S.C. 154(b) by 0 days.

(21) Appl. No.: 09/332,120

(22) Filed: Jun. 14, 1999

Related U.S. Application Data

(63) Continuation-in-part of application No. PCT/FR97/02297, filed on Dec. 15, 1997.

(30) Foreign Application Priority Data

Dec. 13, 1996 (FR) ............................................. 96 15356

(51) Int. Cl.[7] .................................................. A61F 2/00
(52) U.S. Cl. ...................................................... 424/427
(58) Field of Search ............................... 424/427; 623/5, 623/66, 6

(56) References Cited

U.S. PATENT DOCUMENTS

| 4,240,163 | A | | 12/1980 | Galin | |
|---|---|---|---|---|---|
| 4,731,080 | A | * | 3/1988 | Galin | ............................ 623/6 |
| 5,554,187 | A | | 9/1996 | Rizzo, III | |
| 5,888,243 | A | * | 3/1999 | Silverstrini | ..................... 623/5 |

FOREIGN PATENT DOCUMENTS

| EP | 0 335 785 | 10/1989 |
|---|---|---|
| EP | 0 443 809 | 8/1991 |
| EP | 0 563 984 | 10/1993 |
| EP | 0 594 948 | 5/1994 |

OTHER PUBLICATIONS

T. Heyrman et al., "Drug Uptake and Release by a Hydrogel Intraocular Lens and the Human Crystalline Lens", *J. Cataract Refractive Surgery*, vol. 15, No. 2, 1989, pp. 169–175.

O. Nishi et al., "Effect of Indomethacin–Coated Posterior Chamber Intraocular Lenses On Postoperative Inflammation and Posterior Capsule Opacification", *Journal of Cataract & Reflective Surgery*, vol. 21, No. 5, 1995, pp. 574–578.

J. Chapman et al., "Drug Interaction With Intraocular Lenses of Different Materials", *Journal of Cataract & Reflective Surgery*, vol. 18. No. 5, 1992, pp. 456–459.

S. Meski et al. "Use of Methyl Polymethacrylate (PMMA) As a Drug Support", *Proc. 1st World Meeting APGI/APV*, vol. 9, No. 11, 1995, pp. 323–324.

* cited by examiner

*Primary Examiner*—James M. Spear
*Assistant Examiner*—Blessing Fubara
(74) *Attorney, Agent, or Firm*—Young & Thompson

(57) ABSTRACT

The present invention relates to an intra-ocular lens that is made from hydrophilic polymer. An effective amount of medicine is dispersed in the mass of the of the polymer and when implanted in the eye of a subject, the lens releases the medicine into the intra-ocular tissues so that the medicine is in the vicinity of the site where action is needed.

40 Claims, 1 Drawing Sheet

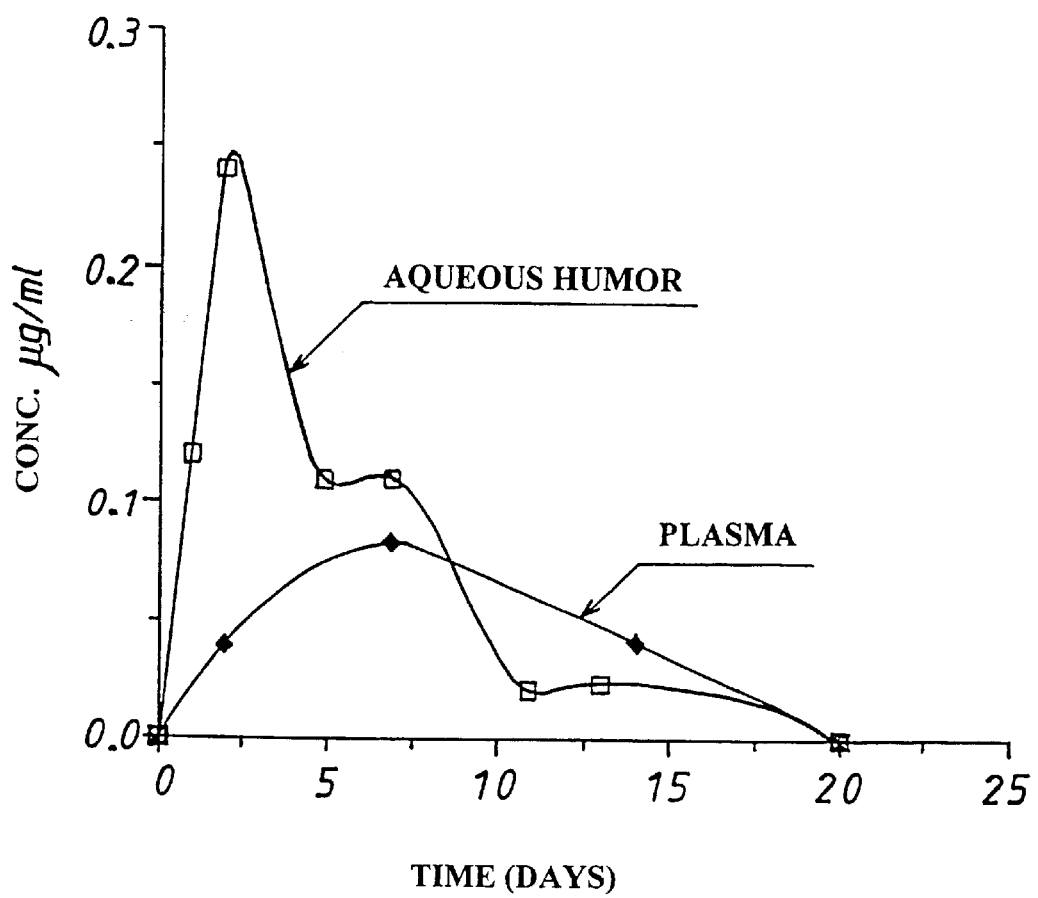

INTRAOCULAR LENS CONTAINING RELEASABLE MEDICATION

This application is a continuation-in-part of international application PCT/FR97/02297 filed Dec. 15, 1997, which designated the United States.

FIELD OF THE INVENTION

The invention concerns a lens made from a hydrophilic polymer intended for implantation in the eye of a subject, in substitution for a defective crystalline lens, during a surgical operation.

Such lenses, known as intraocular lenses (IOL) or intraocular implants and artificial lenses are widely used, in particular to replace an opaque crystalline lens, a condition known as of cataract.

Given the nature of the surgery and the products used, the success such operations depends on the concomitant administration of various medications to limit and attenuate the risks of inflammation.

The corresponding treatment comprises the installation or delivery of appropriate medications, including anti-inflammatory agents, into the eye, two to four times a day, sometimes more, for a long time period, up to a month.

Given that the external membranes of the eye, namely the cornea and the sclera, represent barriers to the passage of medication, the medications must be administered in much higher doses, the excess being either wasted or, which is more serious, drained by the lachrymal liquid and thereafter passing into the systemic circulation, increasing side effects and toxic effects.

The object of the invention is to optimize the therapy by reducing the doses of medication and the risks of side effects by releasing the active principles directly at the site where their action is required, exploiting the fact that, during implantation, an incision is made in the sclera and/or cornea through which the lens is passed.

PRIOR ART

It has been proposed [Journal of Cataract & Refractive Surgery, vol. 21, No. 5, 1995 (Nishi et al): Effect of indomethacin coated posterior chamber intraocular lenses on postoperative inflammation and posterior capsule opacification", EP-A-0,563,984 (Unitika Ltd)] to form a surface deposit of a polymer containing anti-inflammatory or like agents on IOLs so that the medication acts at the precise location where its action is required. However, the quantity of medication is small (the thickness of the coating is necessarily small), it is released into the aqueous humor practically extemporaneously, and its action is hardly prolonged beyond that of medication injected directly into the aqueous humor during the operation. The authors aim to alleviate the immediate reactions of the eye to implantation. These surface treatments do not remove the need for conventional postoperative treatment, which has the drawbacks mentioned above.

EP-A-0 594 948 describes an implant capable of releasing an appropriate medication into the orbit or the eyeball. This implant, which is in the form of an elongate open ring, consists of a biodegradable polymer into the mass of which a medication has been incorporated. The release of the medication is the result of biodegradation. This mode of operation is manifestly incompatible with its incorporation into an intraocular lens, which is implanted permanently and therefore must not be subject to any degradation.

EP-A-0 594 948 claims that the implant it describes could be used as a component part of an intraocular lens. It seems that a component of this kind could not constitute a functional component of the lens (optic and haptic parts) because of its biodegradable, and therefore essentially temporary, nature.

EP-A-0335785 describes polymers for making contact lenses that include the conventional constituents of a hydrogel and a monomer carrying active product that can be copolymerized with the constituents, the monomer including an aryl radical which has a phenol function esterified by a substance with an acid function of the indomethacin type constituting said active product. The monomer can in particular be 4-methacrylamidophenol indomethacin.

SUMMARY OF THE INVENTION

According to an aspect of the invention, a lens is provided for implantation in the eye of a subject, and notably to be substituted for a defective crystalline lens, after extraction, during a surgical operation, which lens is made from a polymer having a predetermined water content, the polymer containing, dispersed in its mass, an effective quantity of a medicated product with appropriate effects, in particular at least partial inhibition of postoperative reactions of the eye, the association of the polymer and the dispersed medicated product being adapted to release the product progressively into the aqueous humor and intraocular tissues.

Because the polymers from which the lenses are made are hydrophilic, the medicated product is released progressively into the aqueous humor and is therefore in immediate range of the sites where its action is required.

In the present context a hydrophilic polymer is a polymer that is able to contain water to enable release of the active products into the aqueous humor. The water content (hydrophilic rate) must be at least 0.20% by weight and preferably at least 0.25% by weight.

Other prior art

The article "Drug Uptake and Release by an Hydrogel Intraocular Lens and Human Crystalline Lens" (Heyrman T. P. et al.), published in Journal of Cataract & Refractive Surgery, vol. 15, No. 2, 1989, discusses the behavior of polymethyl methacrylate or PMMA IOLs compared to the eyes of living beings (rabbits and humans), vis-à-vis medications, in particular anti-inflammatory medications, used for operative and postoperative treatment in cataract surgery. Experiments in vitro and in vivo (on rabbits only) show that the hydrogel absorbs the medications in quantities and at a rate very similar to those for the crystalline lens and that release into the aqueous (and vitreous) humor occurs under similar conditions. The authors conclude that the IOLs studied cannot function as significant reserves of medications in the eye.

The article "Drug Interaction with Intraocular Lenses of Different Materials" (J. M. Chapman et al.) published in Journal of Cataract & Refractive Surgery, vol. 18, No. 5 (1992), complements earlier studies on the interaction of medications with PMMA and polyhydroxyethyl methacrylate (or polyHEMA) IOLs (including the studies reported in the article mentioned previously), by considering other materials and other medications. The article concludes that IOLs cannot deliver sufficient quantities of medications into the eye to modify significantly the kinetics of medications applied topically, sub-conjunctively or intravenously and replace conventional treatments.

The communication "Use of Methyl Polymethacrylate (PMMA) as a Drug Support" El Meski, Beyssac and Aiache; Proc. 1st World Meeting APGI/APV, Budapest 9/11 May 1995, pages 323–324, teaches a method of incorporating a medication into PMMA including drying of the polymer, absorption of a solution of medication in a water/ethanol support comprising 57% by weight of ethanol and final drying (5 days at 110° C.) to evacuate the support.

The step from the teaching of the above communication to the method as defined hereinabove has necessitated, on the one hand, the original concept of using the material of a hard intraocular lens as a reservoir of a medicated product that can be released into the aqueous humor and the surrounding ocular tissues and, on the other hand, the unexpected discovery that the polymer treated in accordance with the teachings of the aforementioned communication could provide a lens optically and surgically suited to long-term substitution for the crystalline lens.

The above communication notes that diffusion of the support into the polymer causes profound changes to the structure of the implant, namely a change from the hard vitreous state to an elastic state analogous to rubber during impregnation, followed by a return to the vitreous state on evaporating the support.

Furthermore, the step from the treatment of a material for hard lenses to that of a material for soft lenses, implanted in a swollen state, involved major unknowns because of the different behaviors of the polymers relative to the solvents likely to constitute the supports and the different rates of diffusion and release specific to these types of polymers.

Our work has shown that for the invention to be effective it is necessary to adapt some operations of the method to the nature of the polymer used for the lens.

Thus, in the case of a polymer for hard lenses, it is necessary to carry out the impregnation at a high temperature on a blank that is then configured or machined into an intraocular lens, in order to have an optical part without surface imperfections and haptic parts that have not been rendered fragile.

In the case of a polymer for soft lenses, it is necessary to sterilize the conformed lens in an isotonic solution containing a chosen concentration of medicated product.

This sterilization process can bring about the impregnation. Alternatively, impregnation follows or precedes sterilization. The concentration of the medicated product is chosen according to the required charge of medicated product in the lens and the reciprocal properties of the polymer and the medicated product.

Other features and advantages of the invention will emerge further from the following description, which is associated with examples and refers to the accompanying drawing.

BIEF DESCRIPTION OF THE DRAWINGS

The single FIGURE constituting the drawing represents the variation with time of the concentration of indomethacin in the aqueous humor and in the plasma of a rabbit implanted with an intraocular lens of the invention.

EXAMPLES OF THE PREFERRED EMBODIMENTS OF THE INVENTION

The first experiments to develop the invention concerned intraocular lenses made from a polymer for hard lenses, namely PMMA. Impregnation of intraocular lenses in accordance with the principles set out in the aforementioned communication of El Meski, Beyssac and Aiache, in their final conformation, caused fragilization of the haptic loops and defects of the dioptric surfaces, as a result of which the lenses were of insufficient quality.

Example 1

Preparation of Hard PMMA Lenses

Disks or semi-finished PMMA blanks were subjected to the following treatment:

Drying of the blanks in an oven at 110° C. for 24 hours to remove internal water;

Immersion, at a high temperature, for 24 hours in a solution of a water/ethanol support containing 57% by weight ethanol, saturated with diclofenac, contained in an opaque container, and maintained at 50° C.;

Rinsing in a 50% water/alcohol mixture;

Drying at 110° C. for 5 days;

Lathe cutting of the blanks into intraocular lenses of the desired configuration;

Polishing the dioptric surfaces; and

Cleaning and sterilization.

Example 2

Preparation of Lenses Impregnated with Indomethacin

PMMA blanks were subjected to the same treatment as in Example 1 except that the water/ethanol support containing 57% ethanol was saturated with indomethacin. Otherwise, the operations were exactly the same.

Various experiments, effected by in vitro release on treated but not conformed IOL blanks showed that the doses of the medicated product contained in the blanks were of the required order of magnitude and that the rate of release into an isotonic solution (comparable in behavior to the aqueous humor) should assure suitable periods of activity.

Example 3

Kinetics of Release in the Rabbit

Three PMMA intraocular lenses impregnated with indomethacin as in Example 2 were each implanted as a substitute for the crystalline lens in one eye of a rabbit, the opposite eye serving as a control.

Samples of the aqueous humor were taken from the treated eyes at DO (before implantation), D7, D14, D21 and D28, i.e. five samples per rabbit.

The indomethacin was measured by high-performance liquid chromatography.

Clinical examination showed that the inflammatory reactions had disappeared by the tenth day from implantation and that the treated eye was identical to the control eye.

In practice, the measured levels of indomethacin in the aqueous humor samples did not yield quantifiable results; only samples 3 and 4 from one rabbit (second and third weeks) contained significant traces, in the order of 0.25 $\mu$g/ml.

It can therefore be concluded that the clinical results are satisfactory and that the doses released or absorbed after release are of the same order as the quantifiable limit. This example emphasizes the benefit of localizing the distribution of the medicated product to the immediate vicinity of the action sites, in order to limit the doses of product delivered into the eye and to avoid the product having any unwanted action in other parts of the body.

The following examples concern soft intraocular lenses, in particular lenses made of polyHEMA (polyhydroxyethyl methacrylate).

Example 4

Impregnation of PolyHEMA

A polyHEMA intraocular lens (containing 38% by weight of water), ready for implantation, was removed from its shipping container, weighed and dried in an oven at 50° C. for 75 minutes. Its mass was only 62% of its original mass, showing that substantially all of the water content had been removed.

The lens was then immersed in a water/ethanol support containing 57% by weight of ethanol, saturated with indomethacin and maintained at 50° C. After 15 minutes immersion the mass of the lens was 115% of the original mass (185% of the mass in the dry state); after 35 minutes it was 130% of the original mass (200% of the mass in the dry state); after 45 minutes it was 150% of the original mass (240% of the mass in the dry state).

Similar experiments using lenses dried for shorter periods showed that the percentage swelling in the water/ethanol support saturated with medicated product depended on the duration and the rate of drying. In this way it was possible to adjust the quantity of medicated product fixed in the lens.

Example 5

Preparation for Implantation

A polyHEMA intraocular lens impregnated as described in Example 4 was washed in a 0.9% NaCl buffer solution (isotonic solution) having a pH of 7.0 and saturated with indomethacin and then placed in an individual shipping container containing the aforementioned buffer solution saturated with indomethacin. The container containing the lens was sterilized in an autoclave at 120° C. for 30 minutes.

Inspection of the lenses at the end of preparation showed that they had not been degraded; they nevertheless had a yellowish tint proving the presence of indomethacin.

Example 6

Kinetics of Release in the Rabbit

A lens prepared as in Example 5 was implanted in the anterior chamber of the right eye of a rabbit. Samples of aqueous humor (approximately 150 µl) and plasma (approximately 2 ml) were taken at random intervals. The indomethacin in the samples was measured by high-performance liquid chromatography (HPLC).

The graph in the single figure of drawing of the present application shows the results of the measurements.

Note that indomethacin was detectable up to the twentieth day. The concentration of indomethacin in the aqueous humor shows a main peak (approximately 0.25 µg/ml) toward the third day and a slight secondary peak (approximately 0.11 µg/ml) toward the seventh day. The concentration in the plasma increased progressively up to the seventh day (approximately 0.9 µg/ml) and then fell at a regular rate until the twentieth day.

Clinical observations showed that the lenses were well tolerated and that the inflammatory reactions disappeared at least as quickly as in Example 3.

Analogous experiments were undertaken with soft intraocular lenses made from other polymers, such as "acrylic polymer". In the present context, "acrylic polymer" means the polymers called this in the field of intraocular lenses, such as a mix of methacrylate and methylmethacrylate.

Even silicone polymers are feasible. By "silicone polymers" it is meant polymers such as conventionally used in the intraocular field and having a minimum water content or hydrophilic rate of at least 0.20%, for example. To this end, the silicone-based polymer is subjected to physical-chemical transformation to shorten the chains so that the polymer in liquid form can be impregnated with the medicated product. Obviously the polymer when so impregnated must be conformed into an intraocular lens.

It was found that, after appropriate drying to remove internal water, impregnation could be carried out during sterilization, the lenses being enclosed in shipping containers containing, as a support, an isotonic solution buffered to pH 7.2 and having a chosen concentration of medicated product.

Sterilization was then performed in an autoclave at 120° C. for 25 minutes.

Example 7

The objective of this example and the following examples was to determine conditions under which effective quantities of the medication could be introduced into soft, polyHEMA IOLs.

Initially, polyHEMA soft IOLs were impregnated by immersing them in a solution saturated with diclofenac (1.8 mg/ml, prepared by dissolving sodium diclofenac in a 0.9% solution of NaCl), at room temperature for 72 hours, carefully rinsed and then released into 1 ml of a 0.9% NaCl solution. After 6 hours, 24 hours and 96 hours, the diclofenac was measured in the release solution by HPLC, after which the IOL was rinsed and, for the intermediate durations, left to release in new solution. The results are shown in the following table. It is understood that the released quantities correspond to the quantities previously absorbed and fixed in the IOLs

| Time | Released quantities in µg/ml | Cumulative or total released quantities in µg/ml |
|---|---|---|
| 6 hours | 127 | 127 |
| 24 hours | 95 | 222 |
| 96 hours | 111 | 333 |

Example 8

The experiment of Example 7 was repeated leaving the IOLs in the saturated solution for 7 days instead of 3. The quantities released were checked after 6 hours and 24 hours. The results are shown in the following table.

| Time | Released quantities in µg/ml | Cumulative or total released quantities in µg/ml |
|---|---|---|
| 6 hours | 122 | 122 |
| 24 hours | 109 | 231 |

It was found that extending the period of impregnation in the saturated solution from 3 days to 7 days had practically no effect on the quantities released, which means that after 72 hours at room temperature the IOL was practically saturated.

The following experiments were intended to determine more precisely the kinetics of release of diclofenac (in vitro experiments).

As previously, the quantities released were measured by sampling the release medium (0.9% neutral NaCl solution) at intervals for measurement and renewing it for a new interval. The samples were taken after 6 hours and 24 hours and then every 24 hours for 14 days in total To approximate the actual (i.e. in vivo) conditions of use more closely, release was effected at 35° C.

The IOLs were impregnated by two different methods. For a first experiment, the IOLs were placed in the solution saturated with diclofenac after which the combination was sterilized at 122° C. for 30 minutes. A second experiment was carried out without sterilization, the IOLs remaining in the diclofenac solution for 24 hours.

The quantities released were substantially the same, to within ±10%, and are set out in the table below in hours (H), days (D) and µg/ml.

| T | 6 H | 24 H | 2 D | 3 D | 4 D | 5 D | 6 D | 7 D | 8 D | 9 D | 10 D | 11 D | 12 D | 13 D | 14 D |
|---|---|---|---|---|---|---|---|---|---|---|---|---|---|---|---|
| Q | 95 | 80 | 40 | 30 | 20 | 18 | 12 | 10 | 10 | 11 | 12 | 14 | 16 | 18 | 20 |

It was noted that the quantity of diclofenac at saturation was practically independent of the impregnation temperature, saturation at room temperature being achieved in less than three days, as shown by the previous experiments. However, saturation was achieved much faster at a higher temperature, which permits simultaneous sterilization and impregnation. Finally, confirming the in vivo experiments previously described, therapeutic coverage extended over at least 15 days, satisfactorily preventing postoperative inflammation.

Example 9

This example involved two sets of five hydrophilic acrylic IOLs. For fixation of the diclofenac, each IOL was placed in a 1.5 mg/ml diclofenac solution and autoclaved for one cycle (120° C. for 30 minutes). To determine quantities fixed during autoclaving, quantities released from the IOLs were measured by successively heating the implants in a double boiler at 97° C., cooling, then leaving them at ambient temperature for a prolonged period, and then repeating this procedure. In each series, Ferrylab stirring was used either prior to or subsequent to the first rest period at ambient temperature. The results are given in the following two tables, respectively for the first and second sets of five IOLs.

Release of impregnated quantities of diclofenac for IOLs 1–5

| Release procedure | IOL 1 | IOL 2 | IOL 3 | IOL 4 | IOL 5 |
|---|---|---|---|---|---|
| Double boiler (1 hour, 97° C.) | 26.93 | 29.42 | 27.51 | 27.68 | 29.11 |
| Ambient temp. (20 hours) | 0.72 | 0.76 | 0.85 | 0.81 | 0.74 |
| Ferrylab stirring (3.30 hours) | 0.14 | 0.19 | 0.19 | 0.17 | 0.18 |
| Ambient temp. (72 hours) | 1.45 | 1.63 | 1.8 | 1.67 | 1.63 |
| Ambient temp. (20 hours) | 0.33 | 0.39 | 0.44 | 0.41 | 0.36 |
| Double boiler (1 hour, 97° C.) | 1.73 | 2.22 | 2.68 | 2.49 | 1.96 |
| Ambient temp. (20 hours) | 0.23 | 0.34 | 0.33 | 0.26 | 0.24 |
| Ambient temp. (20 hours) | 0.17 | 0.23 | 0.24 | 0.26 | 0.17 |
| Double boiler (1 hour, 97° C.) | 0.78 | 1.23 | 1.45 | 1.24 | 0.82 |
| Ambient temp. (20 hours) | 0.11 | 0.18 | 0.32 | 0.18 | 0.21 |
| Ambient temp. (96 hours) | — | 0.37 | 0.37 | 0.37 | 0.23 |
| Double boiler (3 hours, 97° C.) | — | 1.1 | 1.09 | 0.9 | 0.5 |
| Ambient temp. (20 hours) | — | 0.18 | 0.15 | 0.13 | 0.09 |
| Double boiler (1 hour, 97° C.) | — | 0.2 | 0.22 | 0.18 | 0.09 |
| Ambient temp. (20 hours) | — | 0 | 0 | 0 | 0 |
| Cumulative or total quantity | — | 38.44 | 37.64 | 36.75 | 36.33 |

It follows from the total quantities released that the average amount of diclofenac absorbed by each IOL of the series was 37.29 µg.

Release of impregnated quantities of diclofenac for IOLs 6–10

| Release procedure | IOL 6 | IOL 7 | IOL 8 | IOL 9 | IOL 10 |
|---|---|---|---|---|---|
| Ferrylab stirring (3.30 hours) | 12.49 | 12.4 | 15.45 | 14.88 | 16.09 |
| Ambient temp. (20 hours) | 5.05 | 5.47 | 5.35 | 5.41 | 5.73 |
| Double boiler (1 hour, 97° C.) | 10.79 | 11.61 | 11.54 | 10.33 | 11.13 |
| Ambient temp. (72 hours) | 1.89 | 1.96 | 1.88 | 1.89 | 2.12 |
| Ambient temp. (20 hours) | 0.93 | 0.55 | 0.5 | 0.52 | 0.58 |
| Double boiler (1 hour, 97° C.) | 2.2 | 2.57 | 2.2 | 2.25 | 2.58 |
| Ambient temp. (20 hours) | 0.23 | 0.27 | 0.25 | 0.26 | 0.32 |
| Ambient temp. (20 hours) | 0.26 | 0.31 | 0.27 | 0.29 | 0.32 |
| Double boiler (1 hour, 97° C.) | 0.99 | 1.32 | 1.11 | 1.21 | 1.4 |
| Ambient temp. (20 hours) | 0.24 | 0.41 | 0.3 | 0.33 | 0.23 |
| Ambient temp. (96 hours) | 0.34 | 0.4 | 0.35 | 0.39 | 0.42 |

-continued

Release of impregnated quantities of diclofenac for IOLs 6–10

| Release procedure | IOL 6 | IOL 7 | IOL 8 | IOL 9 | IOL 10 |
|---|---|---|---|---|---|
| Double boiler (3 hours, 97° C.) | 0.77 | 1.07 | 0.83 | 1.18 | 1.24 |
| Ambient temp. (20 hours) | 0.18 | 0.14 | 0.1 | 0.15 | 0.17 |
| Double boiler (1 hour, 97° C.) | 0.16 | 0.19 | 0.11 | 0.2 | 0.25 |
| Ambient temp. (20 hours) | 0 | 0 | 0 | 0 | 0 |
| Cumulative or total quantity | 36.52 | 38.67 | 40.24 | 39.29 | 42.58 |

It follows from the total quantities released that the average amount of diclofenac absorbed by each IOL of this series was 39.46 $\mu$g.

Example 10

This example involved impregnation of the IOLs both during and after sterilization to evaluate the quantities of the medicated product which were absorbed by the implants.

Each of three hydrophilic acrylic implants of the type used in Example 9 was first introduced into the container with a 0.9% NaCl solution containing 1.5 mg/ml diclofenac solution. The container was then autoclaved at 122° C. for 30 minutes. After autoclaving, the IOLs were left in their impregnation solution for 10 days at ambient temperature. The procedure described in Example 9 was used to release the absorbed quantities of the diclofenac from the IOLs. The amounts released were respectively 83.57 $\mu$g, 101.66 $\mu$g, 84.16 $\mu$g or an average of 89.79 $\mu$g per implant. These results were over twice as great as those obtained in Example 9 (average about 38 $\mu$g per implant), which involved combining the sterilizing and impregnation steps but which was not followed by extended residence in the impregnation solution.

Example 11

This series of tests was conducted on five hydrophilic acrylic IOLs. The same as those used in Examples 7–10. Each IOL was immersed in a 5 ml of a 1.5 mg/ml diclofenac solution in water sterile for injection for ten days and at ambient temperature without autoclaving prior or after immersion. A simplified procedure for releasing the absorbed quantities of diclofenac was employed which only used double boilers and rest periods but no stirring in a Ferrylab.
The results of these tests are shown in the following table.

| Release procedure | IOL 1 | IOL 2 | IOL 3 | IOL 4 | IOL 5 |
|---|---|---|---|---|---|
| Double boiler (4 hours, 97° C.) | 93.3 | 92.5 | 103.5 | 95.9 | 92.9 |
| Ambient temp. (20 hours) | 0.28 | 0.28 | 0.35 | 0.3 | 0.33 |
| Double boiler (6 hours, 97° C.) | 2.42 | 3.88 | 5.46 | 2.87 | 6.07 |
| Ambient temp. (72 hours) | 0.05 | 0.1 | 0.18 | 0.09 | 0.19 |
| Double boiler (4 hours, 97° C.) | 0.11 | 0.22 | 0.32 | 0.19 | 0.42 |
| Ambient temp. (20 hours) | 0 | 0 | 0 | 0 | 0.05 |
| Double boiler (3 hours, 97° C.) | 0.06 | 0.22 | 0.34 | 0.07 | 0.48 |
| Ambient temp. (20 hours) | 0.05 | 0 | 0 | 0 | 0 |
| Double boiler (1.30 hour, 97° C.) | 0 | 0 | 0.08 | 0 | 0.11 |
| Cumulative or total quantity | 96.27 | 97.2 | 110.23 | 99.42 | 100.55 |

On average, each implant has absorbed 100.73 $\mu$g of diclofenac.

It is noted that relatively large amounts (in excess of 90 $\mu$g) of the active ingredient were absorbed either by autoclaving (Example 10) or by immersion at room temperature (present example). The high level of absorption through autoclaving (Example 10) may be explained by the expansion of the polymeric structure by heating, thereby favoring the penetration of the medicated product (here diclofenac) inside the mesh of the polymeric network but high quantities absorbed by mere immersion at room temperature of the present example was unexpected.

Example 12

It then remained to be shown how quantities of the active ingredient absorbed could be maintained at a desired high level, in excess of 90 $\mu$g and preferably in excess of about 100 $\mu$g, until implantation by the surgeon.

This example included tests on 21 IOLs to ascertain the time it takes for the amount of diclofenac absorbed by the IOL to reach its equilibrium. Each IOL was immersed in 5 ml of 1.5 mg/ml diclofenac solution in deionized water and then sterilized as is conventional, namely at 120° C. for a period of 30 minutes. The sterilized IOLs were then allowed to cool and left in the impregnation solution at room temperature for respective periods of 10 days, 20 days, 35 days, 41 days, 50 days and 65 days. At the end of each of these periods, three IOLs were removed and the quantity of diclofenac was then measured by forced release comprising cycles in a double boiler at 97° C. followed by rest periods until the diclofenac was entirely released from the IOLs.

The amounts of diclofenac released and corresponding to the amounts absorbed for the respective periods are expressed in $\mu$g. These tests show that a substantially equilibrium state with high level of absorbed active ingredient could be achieved by immersion residence of a minimum of 20 days. These results are set out in the following table.

|  | Day 0 | Day 10 | Day 20 | Day 35 | Day 41 | Day 50 | Day 65 |
| --- | --- | --- | --- | --- | --- | --- | --- |
| Test No. 1 | 36.01 | 83.57 | 92.68 | 86.65 | 106.94 | 85.29 | 107.06 |
| Test No. 2 | 31.13 | 101.66 | 95.60 | 100.06 | 108.33 | 114.80 | 98.64 |
| Test No. 3 | 33.59 | 84.16 | 109.99 | 92.18 | 91.90 | 112.90 | 101.41 |
| Average | 33.58 | 89.80 | 99.42 | 92.96 | 102.39 | 104.33 | 102.37 |
| Standard variation | 2.44 | 10.28 | 9.27 | 6.74 | 9.11 | 16.52 | 4.29 |
| Variation coefficient (in %) | 7.27 | 11.45 | 9.32 | 7.25 | 8.90 | 15.83 | 4.19 | t is noted that a level of about 90 µg is achieved after 10 days, and about 100 µg after 20 days and thereafter (except for the dip registered at 35 days) remains substantially constant at a level slightly over 100 µg.

This example establishes that by maintaining the IOLs in the sterilization liquid with the active ingredient for periods of at least 10 days and preferably 20 days equilibrium of the amounts of the active ingredient may be achieved to ensure predetermined, high quantities of the active ingredient at the time of implantation

Example 13

In all the preceding examples the diclofenac was used at concentrations of 1.8 mg/ml or 1.5 mg/ml that is at or only slightly below the saturation level. To avoid the problems attendant to the use of saturated or near saturated solutions, namely instability and risk of precipitation into crystals, other tests have been conducted at lower levels of concentration, namely 0.9 mg/ml, 0.45 mg/ml and 0.225 mg/ml.

In these tests, hydrophilic acrylic IOLs sold by Ioltech, La Rochelle, France, under the trademark Stabibag were first sterilized in their sealed containers in a 0.9% NaCl solution, in accordance with the standard sterilization procedure used for conventional IOLs. The solution contained no active ingredient of any kind.

After sterilization at 121° C. for 30 minutes the containers were opened and the IOLs transferred to other containers which had previously been filled with a 0.9% NaCl solution including respectively 0.9 mg/ml, 0.45 mg/ml and 0.225 mg/ml of diclofenac. The IOLs remained immersed in the impregnation solution for 4 days in each case. Thereafter the absorbed quantities of diclofenac were driven out of the IOLs in double boilers at 97° C. as described above. The quantities fixed were substantially the same as found in Example 7 above, establishing that sterilization prior to impregnation does not negatively effect the quantities diclofenac absorbed by the implant during impregnation. These results are as follows:

70 µg per IOL in the 0.225 mg/ml diclofenac solution after 4 days of immersion;

148 µg per IOL in the 0.45 mg/ml diclofenac solution after 4 days of immersion; and 276 µg per IOL in the 0.90 mg/ml diclofenac solution after 4 days of immersion.

In a second series of tests conducted with an impregnation solution of 0.9% NaCl with 0.9 mg/ml diclofenac under the same conditions as in the first series, except that the residence in the impregnation solution was 49 days. The resulting average quantity of diclofenac fixed by the IOLs was 502 µg diclofenac per implant.

Example 14

A test was carried out on three rabbits which were implanted with hydrophilic acrylic IOLs impregnated by autoclaving in a 1.5 mg/ml diclofenac solution at 120° C. for 30 minutes as described in Example 9 above. The object of this test was to determine the anti-inflammatory effect of diclofenac after a cataract operation. After extraction, the crystalline lens in each eye, the left eye was fitted with an impregnated IOL according to the invention and the right eye with the same kind of IOL with no medicated product therein. The eyes of the rabbit were examined by an operator on day one and microscopically by an ophtalmologist on day 7 and day 14 after the operation. The observations are set out in the following table.

|  | Day 1 after operation | | Day 7 after operation | | Day 14 after operation | |
| --- | --- | --- | --- | --- | --- | --- |
|  | Right eye | Left eye | Right eye | Left eye | Right eye | Left eye |
| Rabbit No. 1 | half closed; red; flow of inflammatory liquid. | open normally; no redness; no flow of inflammatory liquid. | considerable fibrotic deposits. | light fibrotic deposits. | anterior chamber clear; fibrotic deposits on the anterior crystalloid with posterior synechies; fibrotic deposits on the haptic of the IOL. | light fibrotic deposits on the anterior flap on the haptic of the IOL; absence of posterior synechies. |
| Rabbit No. 2 | closed; frequently blinking; redness; flow of | open normally; slight redness; absence of inflammatory liquid. | anterior chamber normal; corneal opacity at the incision; fibrotic deposits in | anterior chamber normal; corneal opacity at the incision; | pigmented deposits on the anterior crystalloid; massive fibrotic deposits around | a few pigmented deposits on the anterior crystalloid; light fibrotic deposits on the haptic; |

-continued

| | Day 1 after operation | | Day 7 after operation | | Day 14 after operation | |
|---|---|---|---|---|---|---|
| | Right eye | Left eye | Right eye | Left eye | Right eye | Left eye |
| | inflammatory liquid. | | the pupillary area. | absence of fibrotic deposits. | each IOL haptic; posterior synechies. | absence of synechies. |
| Rabbit No. 3 | half closed; redness; eye dimmed in inflammatory liquid. | open normally; slight redness; absence of inflammatory liquid. | considerable inflammatory filament which covers the entire IOL optic; haptic in an inflammatory slime; considerable posterior synechies. | slight inflammatory; filament in the optic and on the haptic of the IOL; posterior synechies. | haptic of the implant in a inflammatory slime; posterior synechies. | small inflammatory deposit at the pupil. |

In summary, the preceding table shows that following the operation, the left eye appears normal without apparent inflammatory whereas the right eye is half closed, red and has a flow of inflammatory liquid. At the microscopic examinations on days 7 and day 14, the treated eye shows signs of inflammation in a slight fibrotic deposit on the optic and haptic and some synechies on the right eye of much greater signs of inflammation with systematic fibrotic deposits and frequent posterior synechies. This test establishes a real anti-inflammatory effect of an implant with releasable quantities of diclofenac in the mass of the IOL.

Accordingly, in addition to nonsteroid anti-inflammatory preparations such as diclofenac and indomethacin, tests were carried out with steroid anti-inflammatory products such as dexamethasone.

Impregnation is also envisaged for other medicated products such as antibiotics, antimyotics and other anti-infection products usable to treat ocular or other tissues.

The medicated product can include any necessary active ingredient given the condition of the subject at the time of the operation.

Generally speaking, the experiments showed that the nature of the medicated product had practically no influence on impregnation provided that it was sufficiently soluble in a support able to diffuse into the mass of the polymer.

However, the treatment, in particular sterilization, of the lenses or blanks must obviously not destroy or denature the medicated products and must be adapted if these products are fragile.

In addition to the high temperatures used for impregnation, low temperatures are feasible if, for reasons of stability of the medication (dexamethasone, mitomycin or certain enzymes), impregnation at temperatures below room temperature (for example from 0 to 10° C.) is necessary to preserve the activity of the products.

Impregnation after sterilization is also possible if the sterile implant is brought into contact with the medicated solution only a few minutes, or even a few hours, before implantation, this being true for polyHEMA or acrylic polymer implants with a high hydration power. Sterilization is thereby effected before impregnation which will prevent denaturing the medicated product, especially those likely to become denatured at high temperature.

Finally, the solvents that could be used as impregnation supports include, over and above those described in the examples and the experiments referred to above, isopropyl alcohol and acetonitrile in the group of organic solvents or complex saline solutions in the group of aqueous solvents, such as intraocular irrigation solutions and in particular BSS.

It will be understood that the foregoing description and examples are not limitative of the invention, the scope and spirit of which are defined in the appended claims.

What is claimed is:

1. An intraocular lens comprising an optic part and a haptic part, said intraocular lens being comprised of a hydrophilic polymer having a predetermined water content for implantation in an eye, an effective quantity of a medicated product for at least partial inhibition of postoperative reactions of the eye being dispersed in the mass of the hydrophilic polymer of the intraocular lens, the association of the hydrophilic polymer and the dispersed medicated product being adapted to release the product progressively into the aqueous humor.

2. An intraocular lens according to claim 1, wherein the medicated product is selected from the group consisting of indomethacin, diclofenac and dexamethasone.

3. An intraocular lens according to claim 1, wherein the polymer is polymethyl methacrylate.

4. An intraocular lens according to claim 1, wherein the polymer is a soft lens material selected from the group consisting of polyhydroxyethyl methacrylate, acrylic and silicon polymers.

5. An intraocular lens according to claim 1, wherein the quantity of the medicated product dispersed in the mass of the polymer is at least about 90 µg.

6. An intraocular lens according to claim 1, wherein the quantity of the medicated product dispersed in the mass of the polymer is at least about 100 µg.

7. A method of preparing a hydrophilic polymer intraocular lens containing a medicated product adapted to be released after implantation in an eye, an effective quantity of a medicated product for at least partial inhibition of postoperative reactions of the eye being dispersed in the mass of the polymer, comprising the steps of: removing the greater part of absorbed water from a hydrophilic polymer having a given water content, immersing the hydrophilic polymer in a solution dosed with the medicated product in a medium able to impregnate the hydrophilic polymer, until the solution containing an effective quantity of a medicated product is absorbed in the polymer, conforming the hydrophilic polymer into an intraocular lens for implantation in an eye, implanting the lens, the hydrophilic polymer being sterilized before implantation and allowing the medicated product to be released progressively into the aqueous humor.

8. A method of preparing a hydrophilic polymer intraocular lens containing a medicated product adapted to be released after implantation in an eye, notably in substitution for a defective crystalline lens during a surgical operation, the polymer containing an effective quantity of a medicated product with appropriate effects, for at least partial inhibition of postoperative reactions of the eye being dispersed in the mass of the polymer, comprising the steps of: removing the greater part of absorbed water from the hydrophilic polymer having a given water content, immersing in a solution dosed with the medicated product in a medium able to impregnate the hydrophilic polymer, until the solution is substantially absorbed in the polymer, conforming the polymer into an intraocular lens for implantation in an eye, implanting the intraocular lens, and allowing the medicated product to be released progressively into the aqueous humor and/or intraocular lens and sterilizing the intraocular lens after impregnation.

9. A method according to claim 7, wherein the intraocular lens is rinsed with a solution of the medicated product in the medium.

10. A method according to claim 7, wherein the polymer is selected from the group consisting of polymethyl methacrylate, polyhydroxyethyl methacrylate, an acrylic polymer and a silicone polymer.

11. A method according to claim 7, wherein the polymer is immersed in a solution at an appropriate temperature given the physico-chemical characteristics of the medicated product.

12. A method according to claim 7, wherein the medium is a mixture of water and an organic solvent, selected from the group consisting of solvents including alcohol and a saline solution.

13. A method according to claim 7, wherein the medium is a mixture of water and ethanol, the proportion of ethanol in the solution being 57% by weight.

14. A method according to claim 7, wherein the polymer is a hard lens material and further comprising impregnating the hard lens material blank and then rinsing and conforming the lens blank into an intraocular lens.

15. A method according to claim 14, wherein, after impregnation and rinsing and conforming the blank into an intraocular lens, surface imperfections removed and cleaning and sterilizing the lens.

16. A method of preparing an intraocular lens of soft material containing a medicated product releasable after implantation in an eye, the soft material being a hydrophilic polymer having a predetermined water content, and the lens being implantable in an eye, an effective quantity of a medicated product for at least partial inhibition of postoperative reactions of the eye, being dispersed in the mass of the hydrophilic polymer of the intraocular lens, the method comprising sterilizing and also immersing the intraocular lens in a solution dosed with a medicated product in a medium adapted to impregnate the hydrophilic polymer until absorption of the solution containing an effective quantity of a medicated product in the polymer of the lens.

17. A method of preparing an intraocular lens according to claim 16, wherein the lens is immersed at ambient temperature.

18. A method of preparing an intraocular lens of soft material containing a medicated product releasable after implantation in an eye, the soft material being a polymer having a predetermined water content, and the lens being implantable in an eye, and an effective quantity of a medicated product for at least partial inhibition of postoperative reactions of the eye being dispersed in the mass of the hydrophilic polymer of the intraocular lens, the method comprising the steps of immersing the intraocular lens in a solution dosed with a medicated product in a medium adapted to impregnate the hydrophilic polymer until absorption of the solution in the polymer of the solution containing an effective quantity of a medicated product occurs in the polymer of the lens and sterilizing the lens during immersion in the solution.

19. A method of preparing an intraocular lens according to claim 18, wherein impregnation is continued for at least ten days after sterilization is terminated.

20. A method of preparing an intraocular lens according to claim 16, wherein the concentration of the medicated product in the solution is greater than 1.0 mg/ml.

21. A method of preparing an intraocular lens of soft material containing a medicated product releasable after implantation in an eye, the soft material being a polymer having a predetermined water content, and the lens being implantable in an eye, an effective quantity of a medicated product for at least partial inhibition of postoperative reactions of the eye being dispersed in mass of the hydrophilic polymer of the intraocular lens, the method comprising the steps of: sterilizing the intraocular lens and then immersing the intraocular lens in a solution dosed with a medicated product in a medium adapted to impregnate the hydrophilic polymer until absorption of the solution containing an effective quantity of a medicated product occurs in the mass of the polymer of the lens, and carrying out the immersion at ambient temperature.

22. A method of preparing an intraocular lens according to claim 16, wherein the medium is a mixture of water and an organic solvent, selected from the group consisting of a solvent including alcohol and a saline solution.

23. A method of preparing an intraocular lens according to claim 16, wherein the polymer has a water content of at least 0.20% by weight.

24. A method of preparing an intraocular lens according to claim 16, wherein the polymer has a water content of at least 0.25% by weight.

25. A method of preparing an intraocular lens according to claim 16, wherein the quantity of the medicated product dispersed in the mass of the polymer is at least about 90 $\mu$g.

26. A method of preparing an intraocular lens according to claim 16, wherein the quantity of the medicated product dispersed in the mass of the polymer is at least about 100 $\mu$g.

27. An intraocular lens comprising an optic part and a haptic part, said intraocular lens being comprised of a hydrophilic polymer having a water content of at least 0.20% by weight for implantation in an eye, an effective quantity of a medicated product for at least partial inhibition of postoperative reactions of the eye being dispersed in the mass of the hydrophilic polymer of the intraocular lens, the association of the hydrophilic polymer and the dispersed medicated product being adapted to release the product progressively into the aqueous humor.

28. An intraocular lens according to claim 27, wherein the medicated product is selected from the group consisting of indomethacin, diclofenac and dexamethasone.

29. An intraocular lens according to claim 27, wherein the polymer is polymethyl methacrylate.

30. An intraocular lens according to claim 27, wherein the polymer is a soft lens material selected from the group consisting of polyhydroxyethyl methacrylate, acrylic and silicon polymers.

31. An intraocular lens according to claim 27, wherein the quantity of the medicated product dispersed in the mass of the polymer is at least about 90 $\mu$g.

32. An intraocular lens according to claim 27, wherein the quantity of the medicated product dispersed in the mass of the polymer is at least about 100 $\mu$g.

33. An intraocular lens according to claim 27, wherein the intraocular lens comprises an optical part and a haptic part.

34. An intraocular lens comprising an optic part and a haptic part, said intraocular lens being comprised of a hydrophilic polymer having a water content of at least 0.25% by weight for implantation in an eye, an effective quantity of a medicated product for at least partial inhibition of postoperative reactions of the eye dispersed in the mass of the polymer of the intraocular lens, the association of the polymer and the dispersed medicated product being adapted to release the product progressively into the aqueous humor.

35. An intraocular lens according to claim 34, wherein the medicated product is selected from the group consisting of indomethacin, diclofenac and dexamethasone.

36. An intraocular lens according to claim 34, wherein the polymer is polymethyl methacrylate.

37. An intraocular lens according to claim 34, wherein the polymer is a soft lens material selected from the group consisting of polyhydroxyethyl methacrylate, acrylic and silicone polymers.

38. An intraocular lens according to claim 34, wherein the quantity of the medicated product dispersed in the mass of the polymer is at least about 90 μg.

39. An intraocular lens according to claim 34, wherein the quantity of the medicated product dispersed in the mass of the polymer is at least about 100 μg.

40. An intraocular lens according to claim 34, wherein the intraocular lens comprises an optical part and a haptic part.

* * * * *